United States Patent [19]
Murray, Jr. et al.

[11] Patent Number: 4,653,499
[45] Date of Patent: Mar. 31, 1987

[54] SOLID PHASE ELECTRODE

[75] Inventors: Richard C. Murray, Jr., Palatine; J. Scott Fowler, Lombard, both of Ill.; Mark S. Goorsky, Somerville, Mass.

[73] Assignee: Gould Inc., Rolling Meadows, Ill.

[21] Appl. No.: 699,369

[22] Filed: Feb. 7, 1985

[51] Int. Cl.$^4$ .................................................. A61B 5/00
[52] U.S. Cl. ..................................................... 128/635
[58] Field of Search ......................................... 128/635

[56] References Cited

U.S. PATENT DOCUMENTS 4,340,457 7/1982 Kater ..................................... 128/635
4,519,973 5/1985 Cahalan et al. ....................... 128/635

FOREIGN PATENT DOCUMENTS 0056178 7/1982 European Pat. Off. ............. 128/635

Primary Examiner—William E. Kamm
Attorney, Agent, or Firm—Jeannette M. Walder; G. P. Edgell; E. E. Sachs

[57] ABSTRACT

An electrode for use in miniaturized sensor applications includes an electrically conductive element, a first layer of a salt on the surface of the conductive element having a common cation with the conductive element, a second layer of a second salt coating the first layer, the second layer having a common anion with the first layer, and a membrane covering the second layer, wherein the electrode is completely anhydrous when formed. The membrane may be selected to form either an ion selective electrode or a reference electrode.

41 Claims, 4 Drawing Figures

SOLID PHASE ELECTRODE

BACKGROUND OF THE INVENTION

The invention relates to electrodes and more specifically to miniaturized reference electrodes for in vivo medical applications.

Those concerned with monitoring various ionic or gaseous species in blood typically need to be able to use a miniaturized electrode in vivo to obtain continuous real-time indications of the factors to be monitored. One method of obtaining the necessary information is to use miniaturized electrochemical sensors consisting of a reference electrode and a species-selective electrode in contact with the blood flow of a patient. The most convenient configuration for the electrode pair is to be mounted in a lumen of a catheter which may then be inserted into the bloodstream of the patient through a vein or an artery.

In the past, each individual electrode of a pair of electrodes typically required an aqueous phase within its lumen. This aqueous phase was necessary to make contact between the electrode and the external environment, as well as to provide a reference solution having a fixed concentration of a particular ion required to establish a stable potential for the electrodes. This created a problem in medical applications because it made it difficult to sterilize the electrical sensors by means of the standard procedures using ethylene-oxide gas. When ethylene-oxide is used in the sterilization procedure for any object containing water, a reaction can occur between the ethylene-oxide gas and the water to form ethylene glycol, which is quite toxic. Obviously, this is highly undesirable for medical applications. Furthermore, the ethylene glycol will change the nature of the electrode reference solution. Thus, a need existed to develop an electrode which is completely anhydrous, and therefore sterilizable, and yet would function satisfactorily.

An example of the prior art is described in U.S. Pat. No. 3,856,649 to Genshaw et al. In this patent, a solid-state electrode is described for determining ion concentrations in an aqueous solution. The electrode includes an electrically conductive inner element with a salt disposed on a surface portion thereof having a cation and an anion. The cation is identical to at least a portion of the inner electrode material. A solid hydrophilic layer is in intimate contact with the salt and includes a water-soluble salt of the anion. It is important to note that in the device described in the Genshaw reference, the soluble salt must be mixed with the hydrophilic layer which may or may not be dried after application, but which must be wet in order for the electrode to operate. This is undesirable because such an electrode cannot be sterilized with ethylene oxide while wet, and if dried for sterilization, requires a "wet-up" time before use. Furthermore, the electrode described by Genshaw et al. includes a polyvinyl-chloride hydrophobic layer which the present inventors have found to be highly unsatisfactory for the fabrication of reference electrodes. Plasticized polyvinyl-chloride is unsatisfactory because it appears to be inherently selective to certain ions, in particular $K^+$.

Another ion-sensing device for medical applications is described by Band, D. M. and Treasure, T. *J. Physiol.* (London), 266, 12, 1977 and reprinted in *Ion-Selective Electrode Methodology*, Vol. II, 1979, 58. This is a potassium-sensing catheter for in vivo use, and consists of a potassium-sensing element and a reference electrode which are both inserted in separate lumens of a single catheter. The reference electrode consists of a silver/silver chloride wire that is immersed in a saturated solution of potassium chloride which fills the lumen and which must be periodically flushed and replaced. Obviously, this is inconvenient for both medical personnel and patients and is an undesirable feature because the accuracy of electrical readings using the electrode will suffer if the potassium-chloride solution is not periodically refreshed. This type of arrangement is typical of most in vivo chemical sensing devices. In view of the limitation of these types of prior art devices, a need existed to provide a chemical sensor for in vivo applications which is completely dry and capable of being sterilized with ethylene-oxide gas.

SUMMARY OF THE INVENTION

An object of the subject invention, therefore, was to provide a chemical sensor for in vivo applications which is completely dry and capable of being sterilized with ethylene-oxide gas.

Another object of the subject invention is to provide a device which can be easily fabricated.

Still another object of the subject invention is to provide a reference electrode which can be used as part of an electrochemical sensor for in vivo medical applications and which does not require intermittent flushing of other forms of generally continuous maintenance to insure the accuracy of electrical readings using the electrode.

Yet another object of the subject invention is to provide a reference electrode which is completely dry and does not require a wetting period in order for the electrode to function.

Another object of the subject invention is to provide a truly stable reference electrode which is not sensitive to chemical changes in the external environment.

Another object of the subject invention is to provide an electrode sufficiently small to be inserted into a lumen of a catheter.

Another object of the subject invention is to provide a class of electrodes for selectively sensing specific ionic species.

Another object of the subject invention is to provide a membrane for a reference electrode which is ionically conductive but nonselective.

These and other objects and advantages of the invention, as well as the details of an illustrative embodiment, will be more fully understood from the following description and the drawings.

The invention can be summarized as an electrode for use in miniaturized sensor applications. The sensor includes an electrically conductive inner element and a first salt layer on the surface of the electrically conductive layer having a cation in cation in common with some portion of the electrically conductive inner element. The first salt layer also has an anion. The invention also includes a second salt layer coating the first salt layer, the second salt layer having an anion in common with the first salt layer, the second salt layer being totally anhydrous. In various embodiments of the invention, the electrode can be used as either a reference or sensing electrode. These embodiments are discussed in greater detail below.

DETAILED DESCRIPTION OF THE INVENTION

Figure 1:
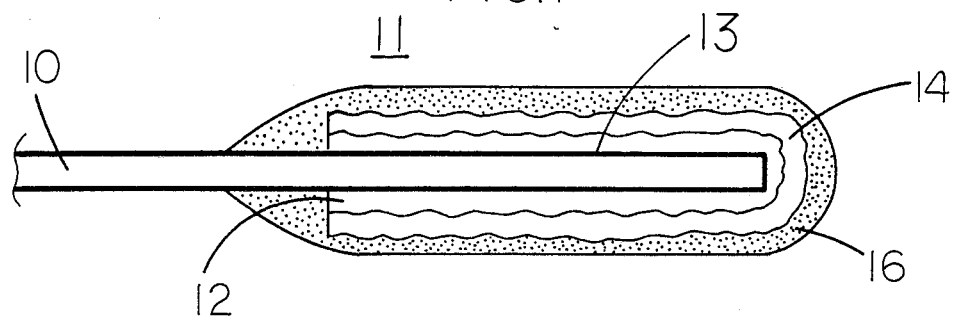
FIG. 1 is a cross-sectional view of a reference electrode illustrating the various layers of material used in a reference electrode in one embodiment of the subject invention.

Referring now to FIG. 1 illustrating the various layers used in an electrode described by the subject invention, it is important to note that the invention comprehends the use of a dry electrode for both reference and sensing applications. The electrode can be either a reference or sensing electrode depending on the type of membrane applied to the outer surface of the electrode. As can be seen in the figure, a wire-type structure 10 is used as the conductive element of the electrode 11. Typically, the conductive element will be formed from silver or a silver alloy. Silver is preferred because it is generally chemically inert since it is a noble element. However, other materials can be used for the inner conductive element for in vivo applications provided that they have the following characteristics: first, they must be nonreactive with body fluids; second, they must be capable of forming an insoluble salt; and third, they must be electrically conductive. Another desirable feature of the material used to form the inner conductive element is that it be capable of forming a reversible electrode with its cation. Other materials that could be used as the inner conductive element are mercury, thallium, and lead. However, each of these materials has serous drawbacks as compared with silver, most notably the fact that the latter two materials are generally more reactive and therefore more likely to become highly toxic in physiological applications, and mercury is less convenient to work with because it is a liquid.

The electrode 11 of the subject invention is formed by applying a first layer 12 composed of salt to the outside surface 13 of the inner conductive element 10 (FIG. 1). This layer is applied by electrochemically oxidizing element 10 in a solution of a soluble salt of an anion which forms a precipitate with the cation of the metal conductor of element 10. In the preferred embodiment, the first salt layer 12, therefore, has a cation in common with the metal of the inner conductive layer. Thus, when the inner conductive element 10 is composed of silver, the first salt layer 12 will form an insoluble silver salt. The first salt layer is required to be a relatively insoluble salt so that the concentration of the cation of the first salt layer 12 will be fixed as a result of an equilibrium with a second salt layer 14 discussed below and yet will not contribute appreciably to the ion current passing through a permeable membrane 16. In the preferred embodiment, the first salt layer is composed of silver chloride formed by the electrochemical oxidation with the silver wire inner conductive element 10 in a dilute solution of HCl. In general, the thickness of the first salt layer should be approximately one third the radius of the element 10. This is to insure that sufficient silver chloride remains after subsequent fabrication procedures discussed below, while at the same time leaving sufficient silver wire to retain mechanical strength or integrity.

In the preferred embodiment, application of the first salt layer upon element 10 can be enhanced by using the procedures discussed below. First, a 0.020" diameter silver wire used as element 10 is annealed prior to the application of the first salt layer. Second, the annealing step is followed by brief etching of the surface of the silver wire in nitric acid for cleaning purposes. Third, after etching, the surface of the wire is further treated by soaking in ammonium hydroxide to remove soluble impurities including silver-oxide. Fourth, the wire is then electrochemically oxidized to apply the first salt layer. The solution of HCl in which the wire is oxidized can vary. Generally, however, the concentration of the solution should be in the range of 0.01 to 0.5 molal. Typically, the current applied to the electrode is in the range of 1 to 100 $mA/cm^2$. In the preferred embodiment, a first cycle of current of 50 $mA/cm^2$ is applied to element 10 for one minute. The polarity of the current is then reversed for one minute to electrochemically reduce a portion of the silver chloride to cause particles of silver to be present in the silver-chloride layer. This provides an integral mixture of silver particles in the silver-chloride salt layer 12. And finally, the polarity of the current is again reversed, the current density is reduced to about 10 $mA/cm^2$, and is applied for approximately 10 minutes.

As can be seen in FIG. 1, a second salt layer 14 is formed upon the first salt layer 12. The purpose of the second salt layer is to provide a fixed concentration of the anion of the first salt layer 12 so as to define the equilibrium concentration of the cation of the first salt layer 12. Another purpose of the second salt layer is to provide majority ionic current carriers through an outer membrane of the electrode as discussed below. A very important consideration in the selection of a material for the second salt layer 14 is that the ionic mobilities of the cation and anion be as nearly equal as possible.

The subject invention comprehends that the second salt layer 14 is applied by dipping the previously described silver/silver chloride covered element 10 into a saturated solution of the salt used to form the second layer 14 of salt. It is advantageous for the salt solution to be at a superambient (elevated) temperature during dipping in order to achieve a fine coating of second-layer salt particles on the surface of the first layer as well as to facilitate the evaporation of water from the electrode surface after dipping. It is desirable to have a fine particle size in order to reduce the overall thickness of the electrode while still maintaining the electrochemical equilibrium as discussed above. This is important to reduce the bulk of the electrode as much as possible.

In the preferred embodiment, the second salt layer 14 is applied upon layer 12 by dipping the element 10 in a saturated solution of potassium chloride. Typically the element and fist salt layer is dipped three times in a solutiom maintained at 80° C. The structure is allowed to dry between dippings. This occurs almost immediately after dipping. The number of dippings is not critical. In some embodiments, a single dipping may be sufficient. Typically, the thickness of the second salt layer is considered to be sufficient when a uniform white layer of potassium chloride is visible on the surface of the electrode.

Although in the preferred embodiment potassium chloride is used to form the second salt layer, other materials can be used. For example $KNO_3$, $NH_4NO_3$, or RbCl may be used as the second salt layer 14, although in the cases of $KNO_3$ and $NH_4NO_3$, a second soluble salt containing the chloride anion would need to be present at some small but finite concentration. The main requirements of the material chosen to form the second salt layer 14 are: first, the cation and anion should have nearly the same ionic mobility; second, the salt should be readily soluble in water (water solubility is important to be able to provide a high concentration of the majority current carriers); and third, it should contain the anion of the first salt layer. This second salt layer 14 can be composed of a mixture of two or more salts. When used to form a sensing electrode, the composition of this second salt layer 14 may require the inclusion of other ionic species with particular properties (e.g., identity with the ion being sensed). This will be discussed in greater detail below.

When the subject invention is used as a reference electrode, a hydrophobic outer layer 16 is formed upon layer 14. The outer layer is a membrane which is not selective with respect to ion transport by a particular ion, thus allowing the structure to operate as a reference electrode. In the preferred embodiment, the substance used as the membrane is plasticized or unplasticized cellulose acetate butyrate. The membrane is applied by dipping the structure containing the first and second salt layers into a solution of the membrane material in a nonaqueous solvent such as tetrahydrofuran. The thickness of the membrane layer ranges between 0.05 and 0.8 mm. In the preferred embodiment, the thickness is no critical provided that the membrane substance completely covers the internal salt layers. It is also necessary that the membrane be sufficiently thick to avoid the presence of pinholes and to provide sufficient mechanical stability. However, if the membrane becomes too thick, the electrode resistance and its sensitivity to electrical noise will become excessively high.

It should be noted that other materials may be used as the membrane material when the subject invention is used as a reference electrode. Other materials include any plasticized or unplasticized polymeric material taken from the group consisting of cellophane, collodion, or cellulosic derivatives such as cellulose acetate butyrate, ethyl cellulose, cellulose acetate, cyanoethylated cellulose, cellulose propionate, or cellulose tridecanoate. However, cellulose acetate butyrate or ethyl cellulose plasticized with didecylphthalate is preferred.

Figure 3:
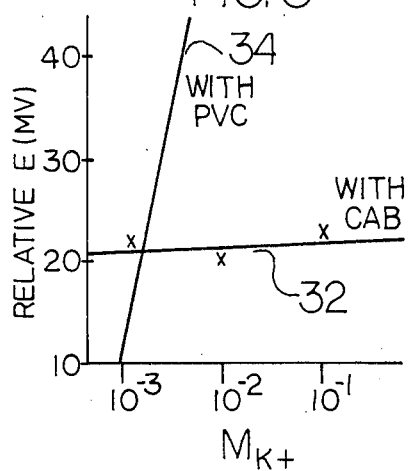
FIG. 3 is a graph illustrating the insensitivity of the response of a reference electrode of the subject invention to changes in potassium concentration and a comparison of the insensitivity of the subject invention electrode with that of prior-art electrodes.

Referring now to FIG. 3 which shows a plot of the response 32 of a reference electrode formed using the techniques described herein to changes in the concentration of potassium chloride in an aqueous solution relative to an electrode of fixed potential. As can be seen in the figure, there is no response to changes in the concentration of the solution for the subject electrode. Also shown in FIG. 3, is a plot of the response 34 of an electrode made using a polyvinyl chloride membrane of the type described in U.S. Pat. No. 3,856,649 to Genshaw et al. As can be seen from the figure, the electrode made using a polyvinyl chloride membrane shows a substantial response to changes in the potassium-ion concentration.

The electrode 11 of the subject invention can be used as a sensing electrode as well as a reference electrode provided that a different membrane is used. In a sensing application, the outer membrane must be selective to the particular ion to be monitored. For instance the subject electrode can be used to monitor a multitude of chemical species such as the ions of potassium sodium ammonium, calcium, magnesium, or any other of the various ionic species.

Two key features of the invention which are discussed in greater detail below are that the electrode 11 is basically anhydrous, and does not have to be intentionally hydrated to function, and that it produces a thermodynamically well-defined potential. The electrode has a thermodynamically well-defined potential because all phases involved in the electrode reaction are clearly defined and are mutually at equilibrium.

When the electrode is used to sense potassium, the outer layer 16 could be formed from silicone rubber or plasticized polyvinyl chloride, polyhydroxyethyl methacrylate or a number of other similar hydrophobic polymeric materials. Any of the polymers used may be plasticized using compatible plasticizers, such as didecylphthalate in the case of polyvinyl chloride, or any of the class of phthalic acid derivatives, citric acid derivatives, adipic acid derivatives, or sebacic acid derivatives, among others. In order to achieve selectivity for potassium ions, valinomycin, crown ethers or some similar specific complexing agent is added to the solution of the polymeric membrane material before the electrode is coated. Depending on the particular ion to be monitored, a variety of materials may be used for the ion-selective membrane. For example, in one embodiment of the subject invention, a mixture may be formed using polyvinyl chloride, didecylphthalate, and a complexing agent selective to said specific ionic species. In the preferred embodiment, a 47.5% polyvinyl chloride, 47.5% didecylphthalate, 5% Valinomycin membrane is used to selectively measure $K^+$ concentrations.

Figure 2:
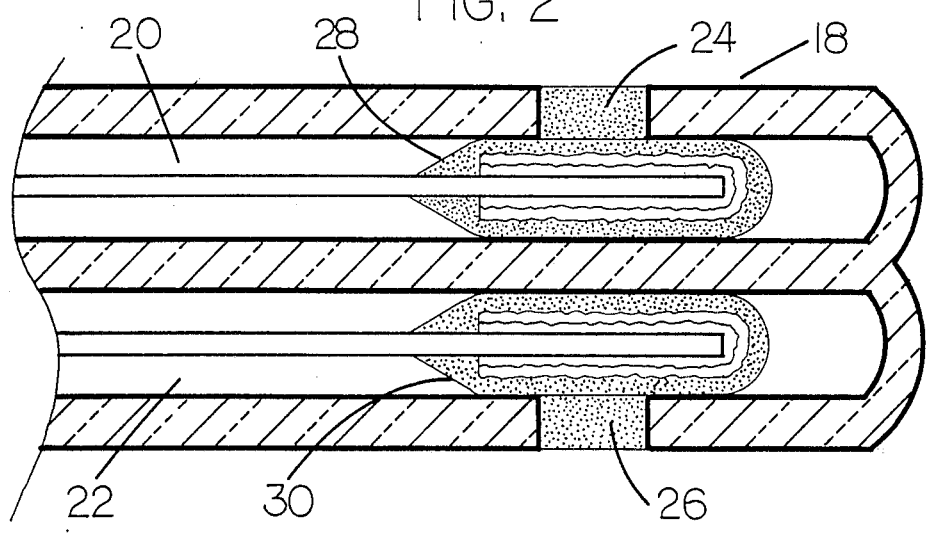
FIG. 2 is a view similar to FIG. 1, illustrating one embodiment of the subject invention in which a reference electrode and a sensing electrode are inserted in separate lumens of a catheter.
Figure 4:
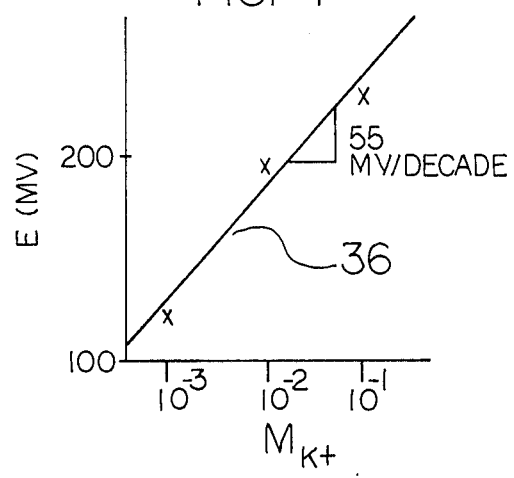
FIG. 4 is a graph illustrating the $K^+$ response of a reference electrode and $K^+$ sensing electrode, mounted in a cathether, to changes in the $K^+$ concentration.

Referring now to FIG. 4 which shows a plot of the response characteristic of an electrode pair consisting of a potassium-selective electrode 30 relative to a reference electrode 28, both constructed as described in the subject application, and mounted in a catheter as shown in FIG. 2. FIG. 4 demonstrates that the sensitivity of the electrode pair to changes in the potassium concentration is nearly equal to the theoretical value, being 55 mV/pK+ as compared to the theoretical value of 59 mV/pK+.

In a similar manner, when the electrode 11 is used to sense other ions, an appropriate complexing agent specific for that particular ion is added to the polymeric solution in place of valinomycin or crown ether.

It is important to note that in the subject invention, the electrode is completely anhydrous when formed. This distinguishes it from other devices in the field which typically require aqueous solutions of hydrophylic layers which absorb and retain water. Although the detailed mechanism of operation of the subject electrode is not yet completely understood, it is believed that trace amounts of water are absorbed through the membrane during operation. This produces a saturated solution of the second layer salt; the solution composition will remain fixed as long as some solid from the second salt layer 14 remains.

Another important feature of this type of sensing electrode compared with prior art coated-wire electrodes is that all phases and interfaces of sensors fabricated in accordance with the techniques described herein are thermodynamically well-defined so that the potential of the electrode has thermodynamic significance. The potential of the prior-art coated wire sensor is determined by capacitive effects and is therefore less stable and reproducible.

Referring again to FIG. 2, in one embodiment of the invention, a reference electrode and an ion-selective sensing electrode are inserted in separate lumens on a single catheter. A catheter 18 has a first and second lumen 20, 22. Each lumen has an orifice 24, 26 to expose a portion of each lumen to the environment. A reference electrode 28 is inserted in one catheter of lumen 20, and a sensing electrode 30 is inserted in the other lumen. After each of the electrodes are inserted, each orifice is filled with a membrane material identical to the membrane material used for the specific electrode within the lumen. The solvent for the membrane solution is chosen such that it will partially dissolve the material of the catheter during application thereby forming a sealing bond between the membrane and the catheter.

It is also possible to insert both electrodes into the same lumen if care is taken to insulate the two electrodes and electrical conductors from one another. Thus, it is possible to form a sensing device which is specific for a given ionic species, can be sterilized using ethylene oxide or gamma sterilization, and is suitable for in vivo applications. In addition, the electrode sensing devices formed using the techniques of the subject invention are simple to prepare and convenient to use. Since sensors formed using the subject invention can be easily sterilized without fear of producing harmful toxins, such as ethylene glycol, such sensors are particularly appropriate for medical applications.

A major advantage of the subject invention is that electrodes formed using the techniques described herein can be sterilized for medical purposes by various techniques including the use of radiation, gas, ultraviolet light and steam.

Another advantage of the subject invention is that since sensors made using this technique contain only solid salt phases and polymer membranes, the technique lends itself particularly to the fabrication of extremely small sensing devices. For example, such sensor can be incorporated into electronic devices such as field effect transistors. It is further envisioned that sensors fabricated using the techniques described herein could even be sufficiently miniaturized to be placed within a hypodermic needle or medical cannula.

Although the invention has been described and illustrated in detail, it is to be clearly understood that the same is by way of illustration and example only, and is not to be taken by way of limitation; the spirit and scope of this invention being limited only by the terms of the appended claims.

We claim:

1. An electrode for use in miniaturized sensor applications, comprising;
   an electrically conductive element;
   a first layer of salt on the surface of said electrically conductive element, said first layer having a cation in common with some portion of said electrically conductive element;
   a second layer consisting essentially of at least one salt providing a coating on said first layer, said second layer having an anion in common with said first salt layer; and
   a membrane surrounding said second layer; wherein said membrane is selected from the group consisting of solution permeable membranes and ion-selective membranes;
   wherein the electrode is completely anhydrous when formed.

2. An electrode as recited in claim 1, wherein: said second salt layer is the product of a dipping process in which said conductive element and said overlying first salt layer are dipped into a saturation solution of said salts of which said second layer is to be formed.

3. An electrode as recited in claim 2, wherein:
   said saturated solution of said second salt layer is at a superambient temperature during said dipping.

4. An electrode as recited in claim 3, wherein:
   said second salt layer includes a majority component selected from the group consisting of KCl, KNO$_3$, NH$_4$NO$_3$, and RbCl.

5. An electrode as recited in claim 4, wherein:
   said second salt layer includes a minority component for establishing said anion in common with said first salt layer.

6. An electrode as recited in claim 3, wherein:
   said second salt layer is formed of anhydrous KCl.

7. An electrode as recited in claim 1, wherein said membrane is a solution permeable membrane such that said electrode is a reference electrode.

8. An electrode for use in miniaturized sensor applications comprising:
   an electrically conductive element;
   a first layer of a first salt on the surface of said electrically conductive element, said first salt having a cation in common with some portion of said electrically conductive element;
   a second layer consisting essentially of at least one second salt providing a coating on said first layer, said second salt having an anion in common with said first salt; and
   a membrane surrounding said second layer, wherein said membrane is formed of a hydrophobic polymeric material.

9. An electrode as recited in claim 8, wherein:
   said polymeric material is selected from the group consisting of cellophane, collodion, and cellulosic derivatives such as cellulose acetate butyrate, cellulose acetate, cyanoethylated cellulose, cellulose propionate, cellulose tridecanoate, and ethyl cellulose.

10. An electrode as recited in claim 9, wherein: said membrane is the product of a dipping process in which said conductive element and overlying first and second salt layers are dipped into a solution of said polymer and a nonaqueous solvent which will dissolve the polymer without dissolving said first and second salt layers.

11. An electrode as recited in claim 8, wherein:
    said membrane is formed of cellulose acetate butyrate.

12. An electrode as recited in claim 8, wherein:
    said membrane is formed of ethyl cellulose.

13. An electrode as recited in claim 8, wherein:
    said membrane has a thickness of 0.05 to 0.8 mm.

14. An electrode as recited in claim 1, wherein:
    said electrically conductive inner element is at least partially formed of silver;
    said first salt layer is formed of AgCl; and
    said second salt layer is formed of KCl.

15. An electrode as recited in claim 1, wherein said membrane is an ion-selective membrane such that said electrode is an ion-selective electrode.

16. An electrode as recited in claim 15, wherein:
said membrane is formed of a plasticized hydrophobic polymeric material.

17. An electrode as recited in claim 16, wherein:
said polymeric material is selected from the group of materials consisting of silicone rubber, polyvinyl chloride, polystyrene, polyhydroxyethylmethacrylate, polyvinylidene chloride, and polyurethane.

18. An electrode as recited in claim 15, wherein: said membrane is the product of a dipping process in which said conductive element and overlying first and second salt layers are dipped into a solution of said polymer and a nonaqueous solvent which will dissolve the polymer without dissolving said first and second salt layers.

19. An electrode as recited in claim 15, wherein:
said membrane includes a plasticizer selected from the group of materials consisting of phthalic acid derivatives, citric acid derivatives, adipic acid derivatives, and sebacic acid derivatives.

20. An electrode as recited in claim 15, wherein:
said membrane is formed of a mixture of polyvinyl chloride, didecylphthalate, and a complexing agent selective to said specific ionic species.

21. An electrode as recited in claim 20, wherein:
said membrane has a thickness of from 0.05 to 0.8 mm.

22. An electrode as recited in claim 15 further comprising a catheter wherein said electrode is positioned in a lumen of said catheter, said catheter lumen having an orifice for exposing a portion of said electrode in juxtaposition with said orifice to the environment.

23. An electrode as recited in claim 22, further comprising:
means for attaching said electrode to said lumen around said orifice and for sealing the inside of said lumen from the ambient environment.

24. An electrode as recited in claim 23, wherein:
said means for attaching and sealing includes a second membrane formed from the same material as said membrane, said second membrane formed such that said membrane and said second membrane form a contiguous layer, said second membrane also forming a bond with said catheter to seal the inside of said lumen from the environment.

25. An electrode as recited in claim 24, wherein:
said second membrane is formed of plasticized hydrophobic polymeric material.

26. An electrode as recited in claim 25, wherein:
said polymeric material of said second membrane is selected from the group of material consisting of silicone rubber, polyvinyl chloride, polystyrene, polyhydroxyethylmethacrylate, polyvinylidene chloride, and polyurethane.

27. An electrode as recited in claim 25, wherein:
said second membrane is formed of a mixture of polyvinyl chloride, didecylphthalate, and a complexing agent selective to said specific ionic species.

28. An electrode as recited in claim 27, wherein:
said electrically conductive inner element is at least partially formed of silver;
said first salt layer is formed of AgCl; and
said second salt layer is formed of KCl.

29. An electrode for medical applications comprising:
an electrically conductive inner element;
a first salt layer on the surface of said electrically conductive layer, said first layer having a cation in common with some portion of said electrically conductive inner element;
a second salt layer consisting essentially of at least one salt coating said first salt layer, said second salt layer having an anion in common with said first salt layer; and
a membrane surrounding said second layer, wherein said membrane is selected from the group consisting of solution permeable membranes and ion-selective membranes, wherein the electrode is completely anhydrous when formed; and further comprising
a catheter surrounding a portion of the electrode.

30. An electrode as recited in claim 29, wherein said membrane is a solution permeable such that said electrode is a reference electrode.

31. An electrode as recited in claim 30, wherein:
said electrode is positioned in a lumen of said catheter, said catheter lumen having an orifice for exposing a portion of said electrode in juxtaposition with said orifice to the ambient environment.

32. An electrode as recited in claim 31, further comprising:
means for attaching said electrode to said lumen around said orifice and for sealing the inside of said lumen from the environment.

33. An electrode as recited in claim 32, wherein:
said means for attaching and sealing includes a second membrane formed from the same material as said membrane, said second membrane formed such that said membrane and said second membrane form a contiguous layer, said second membrane also forming a bond with said catheter to seal the inside of said lumen from the environment.

34. A reference electrode for medical applications comprising:
an electrically conductive inner element;
a first layer of a first salt on the surface of said electrically conductive element, said first salt having a cation in common with some portion of said electrically conductive element;
a second layer consisting essentially of at least one second salt providing a coating on said first layer, said second salt having an anion in common with said first salt; and
a membrane surrounding said second layer, wherein said membrane is formed from a hydrophobic polymeric material.

35. An electrode as recited in claim 34, wherein:
said polymeric material is taken from the group consisting of cellophane, collodion, for cellulosic derivatives such as cellulose acetate butyrate, cellulose acetate, cyanoethylated cellulose, cellulose propionate, cellulose tridecanoate, or ethyl cellulose.

36. An electrode as recited in claim 34, wherein:
said membrane is formed of cellulose acetate butyrate.

37. An electrode as recited in claim 34, wherein:
said membrane is formed of ethyl cellulose.

38. An electrode as recited in claim 31, wherein:
said electrically conductive inner element is at least partially formed from silver;
said first salt layer is formed from AgCl; and
said second salt layer is formed from KCl.

39. A sensing device for selectively monitoring ionic activity, comprising:

a catheter having at least one lumen;

a first electrode disposed within said lumen, said lumen being provided with a first orifice to expose a portion of said first electrode to the environment, said first electrode including:

an electrically conductive element; a first layer of a salt on the surface of said conductive element, said first layer having a cation in common with said conductive element;

a second layer consisting essentially of at least one salt coating said first layer, said second layer having anion in common with said first salt layer; and a membrane surrounding said second layer, said membrane being a solution permeable membrane such that said first electrode is a reference electrode;

wherein said first electrode is completely anhydrous when formed;

a second electrode disposed within said lumen, said lumen being provided with a second orifice to expose a portion of said second electrode to the environment, said second electrode including;

an electrically conductive element;

a first layer of a salt on the surface of said conductive element, said first layer having a cation in common with said conductive element;

a second layer consisting essentially of at least one salt coating said first layer, said second layer having an anion in common with said first salt layer; and a membrane surrounding said second layer, said membrane being an ion-selective membrane such that said second electrode is an ion-selective electrode;

wherein said second electrode is completely anhydrous when formed.

40. A device as recited in claim 39, wherein:

said first and second electrodes are in the same lumen of said catheter, said electrodes being electrically insulated from each other.

41. A device as recited in claim 39, wherein:

said first and second electrodes are in separate lumens of said catheter.

* * * * *